United States Patent [19]

Arias

[11] Patent Number: 4,689,223

[45] Date of Patent: Aug. 25, 1987

[54] METHOD OF TREATING THE SYMPTOMS OF THE COMMON COLD

[75] Inventor: Fredo Arias, Mexico City, Mexico

[73] Assignee: T & R Chemicals, Inc., Clint, Tex.

[21] Appl. No.: 855,378

[22] Filed: Apr. 24, 1986

[51] Int. Cl.$^4$ ...................... A61K 33/04; A61K 33/06
[52] U.S. Cl. ..................................... 424/154; 424/162
[58] Field of Search ................................ 424/162, 154

[56] References Cited

U.S. PATENT DOCUMENTS

| | | | |
|---|---|---|---|
| 3,149,035 | 9/1964 | Riegelman | 514/653 |
| 3,169,092 | 2/1965 | Petraglia et al. | 514/653 |
| 4,327,083 | 4/1982 | Alvarez | 424/162 |
| 4,401,654 | 8/1983 | Alvarez | 424/162 |
| 4,581,376 | 4/1986 | Marci | 514/653 |

OTHER PUBLICATIONS

Goodman & Gilman—"The Pharmacological Basis of Therapeutics, 5th Ed., 1975, pp. 338, 505, 506, 529, 610, 611.

*Primary Examiner*—Leonard Schenkman
*Attorney, Agent, or Firm*—Nixon & Vanderhye

[57] ABSTRACT

This invention relates to the treatment of the common cold either by ameliorating the symptoms of the common cold or by preventing the rhinoviruses from causing colds or by preventing from the cold symptoms to from worsening. The invention includes the treatment of the common cold or head cold in mammals, especially man, and describes methods of treatment and pharmaceutical compositions for use in carrying out such treatments.

13 Claims, No Drawings

METHOD OF TREATING THE SYMPTOMS OF THE COMMON COLD

BACKGROUND OF THE INVENTION

Common colds appear to be caused by a number of viruses or at least a number of strains of viruses which explains the remarkably transient immunity to colds and the fact that reinfection can take place within as little as three weeks of an apparent recovery. No ailment is quite so universal as the common cold and, indeed, it is probably the commonest of all infectious diseases.

An institution that has played a major role in the investigation of the cold is The Medical Research Council, Common Cold Unit, Salisbury, England. Investigations and tests at MRC during the past forty years have proven that the common cold is caused by rhinoviruses that enter the body mainly by the nostrils, and are usually transmitted by an infected person, sometimes by a simple handshake, that will often carry the virus to the facial cavities and there contact the mucus membranes. A good sneeze from an infected person in a public place will disseminate a vast number of droplets among those present, some of whom will quite likely acquire an upper respiratory tract infection.

The infection produced by the rhinovirus is an acute one, and like other acute infections, it may clear up in the course of only a few days. Frequently, however, secondary invaders follow upon the primary infection, and these convert an otherwise acute infection into a chronic disease which may drag on for several unpleasant weeks. These secondary invaders attack first the nose and throat and may later spread to the larynx, trachea, bronchi and up into the sinuses which open into the nose. For the first day or so, the mucus membrane lining of the nose and throat is swollen, red and dry, giving the all too well known symptoms of feeling "stuffed-up". Soon the nose secretes a watery fluid which runs from the nose continually. Secondary invaders change the nature of the inflammation from a watery secretion to one that is more purulent which may continue to be discharged for several weeks.

Folk medicine through the years has suggested the uses of endless numbers of remedies, including pine-needle, honeysuckle, chrysanthemum and licorice teas. Some people believe in sweating the cold out, or taking a hot alcoholic beverage and aspirin before going to bed at night are useful, although there is a theory that aspirin aggravates the common cold.

More recent treatments for the common cold include the use of topically-applied sympathomimetic drugs which exert a vasoconstrictor action directly on the mucus membrane to which they are applied. An example of such a drug is epinephrine, although other more recently developed longer-acting drugs are preferred. All of these have the disadvantage that their use may be followed by "after congestion" and that prolonged use over a period of time often results in chronic rhinitis. Ephedrine and pseudoephedrine, also sympathomimetic drugs, have been given orally as nasal decongestants either by themselves or in combination with a variety of other agents including antihistamines, analgesics, caffeine, antitussives or antimuscarinic drugs. Of this last-mentioned category, atropine and belladonna alkaloids are the most commonly used to reduce secretions in both the upper and lower respiratory tract, including reducing the volume of bronchial secretion. It is recognized that this therapy does not affect the natural course of the condition for which the drugs are administered; see Goodman and Gilman. The Pharmacological Basis of Therapeutics (1975), at page 529. All of these drug substances discussed above are used to treat the symptoms of the infection and, to make the patient more comfortable while the infection runs its normal course of several days to over a week.

Despite extensive discussions in the literature of folk medicine and current therapeutics, little has been written about the fact that some individuals' nasal acid system destroys invading rhinoviruses. These germ-destroying properties of such acidic conditions are particularly useful in the nasal passages which, under normal conditions, provide secretions that are only slightly on the acid side. It is believed that this acidic-type environment makes the nasal passages and mucus membranes an inhospistable environment for invading rhinoviruses.

DESCRIPTION OF THE INVENTION

I have discovered, and hereby disclose, a means for adjusting the pH of the nasal cavity, including the involved mucus membranes, by administering to that cavity ions of a family of pharmaceutical agents defined in more detail below. These agents and this course of administration treats the preliminary symptoms of the common cold and thus, I believe, serve to abort development of these initial symptoms into a full-blown rhinovirus common cold infection.

While not wishing to bound by any particular theory or mode of operation, it appears that to a certain degree the normal (non-viral infected) state acidity in the nose is effective to prevent propagation of invading rhinoviruses. However, there comes a time when nasal acidity is no longer sufficient to inhibit rhinovirus replication. It is at this point that the nasal secretions shift from acidity to alkalinity. An alkaline environment is hospitable and facilitates propagation of these rhinoviruses and this, in turn, initiates the all too well known syndrome developing into a head cold or common cold. In changing from acidic to alkaline conditions, the body attempts to defend itself, via a pseudo "immunization" (for lack of a more precise word) but in the meantime, the cold symptoms almost always continue to mount and may last from 4 to up to 14 days to subside—assuming, of course, that no further complications, such as secondary invaders, occur.

Onset of acidity/alkalinity change—almost every individual feels certain symptoms that foretell the person that the symptoms of a cold are about to set in. These may manifest themselves in many forms, depending upon the individual, but it usually starts as an itching sensation inside of the nose, often accompanied by sneezing. It is believed that these preliminary symptoms at the outset of a cold are the turning point from the normal acidity to alkalinity conditions in the mucus membranes lining the nasal passages and sinus cavities. The present invention is based on the discovery that when the released ions of a family of pharmaceutical agents, identified in more detail below, are administered to a mammal, including man, in the affected area, these preliminary cold symptoms do not further develop, a full blown cold does not result and the person receiving such therapy is spared many unpleasant days and nights of discomfort.

In a first aspect of my invention I have discovered that sodium bisulfite, either as such or in an aqueous solution of sulfite ions ($SO_3^-$), is useful in the treatment of the symptoms of the common cold and related conditions when administered to humans in a suitable form or vehicle such as in an aqueous dilute solution.

This invention thus includes the treatment and amelioration of symptoms of the progressive onset of rhinovirus infection of a person suffering from such an infection. Conceptually the method results in an adjustment of the pH of the person's nasal mucosal membrane. This is accomplished by administering to the person in the nasal mucosa, or otherwise, a pH-adjusting and rhinovirus-inhibiting quantity of an isotonic, buffered solution of a sulfite or bisulfite salt, such as the sodium, potassium, calcium or magnesium salts. Preferably the salt administered is sodium bisulfite or sodium metabisulfite, and the isotonic, buffered solution is administered dropwise either as a nasal solution or it is sprayed into the patient's nostrils as a nasal spray. The concentration of active ingredient in the solution ranges from 1 to 10%, preferably 3-7%, and is generally about 5%.

In another aspect, the invention also includes a method of treating the symptoms of the common cold in a person having such symptoms by administering to that person a symptom-alleviating amount of a compound which, in aqueous solution, furnishes sulfite ions, bisulfite ions or both.

Also included within the invention is a pharmaceutical composition for installation into the nose of a patient having the common cold for treating the symptoms of that common cold. The composition consists essentially of from about 1 to about 10 weight percent of sodium bisulfite or sodium metabisulfite. The balance of the solution is a buffered, isotonic and optionally sterile aqueous carrier suited for nasal installation. Containers adapted to deliver drop-wise or by spray such a pharmaceutical composition are also described.

Sodium bisulfite, usually shown by formula to be $NaHSO_3$, has been used for many commercial purposes, as a preservative for prevention of the deterioration of liquids, such as food-stuffs and pharmaceutical solids and solutions, and has been used medically externally for parasitic skin diseases and internally as a gastrointestinal antiseptic.

The sodium bisulfite of commerce consists chiefly of sodium metabisulfite, $Na_2S_2O_5$, and for purposes of this invention such is believed to possess the same properties as (and to be equivalent to) the true sodium bisulfite when dissolved in an aqueous solution.

The use of sodium bisulfite and metabisulfite in the treatment of hypertension is described in U.S. Pat. No. 4,327,083 and is also described as an antithrombotic agent useful for prolonging both prothrombin time (PT) and partial thromboplastin time (PTT) of blood or blood plasma in U.S. Pat. No. 4,401,654. The use of sulfite and/or bisulfite ions for the treatment of epilepsy and epileptic conditions as well as arthritis and arthritic conditions are described in U.S. Pat. No. 4,532,131. To the best of my knowledge, sulfite and bisulfite ions have not previously been used or otherwise described in the art for the treatment of the symptoms of the common cold (rhinovirus-originated) or for preventing further common cold symptoms from developing.

More particularly, this invention concerns a process for treating the symptoms of the common cold caused by rhinoviruses wherein there is administered a chemical agent comprising at least one compound which in aqueous solution that furnishes at least one ion selected from the group consisting of bisulfite (which is preferred) and sulfite, the ion being present in a pharmaceutically effective amount. Inorganic salts of sulfurous acid are suitable agents for practicing the invention, such as the pharmaceutically acceptable and existing compounds of the alkali metal, alkaline earth metal and ammonium salts of bisulfite and sulfites, including metabisulfites. Preferred are the sodium, potassium, calcium and magnesium salts.

Administration of the solution can be accomplished by oral ingestion, injection, absorption, or otherwise as desired. Injections can be accomplished intravenously, intramuscularly, intraperitoneally, subcutaneously or otherwise. A preferred method of administration is with a spray or nosedropper containing an aqueous solution of any pharmaceutical agent capable of releasing sulfite and/or bisulfite ions, by spraying into or dropping down drops in one of the nostrils of a patient in a lying position. After one minute the same administration is repeated in the other nostril. After and additional minute, the patient can blow his or her nose (both nostrils). When the composition is first applied in the manner indicated, there is a transitory burning sensation inside the sinus area and possibly as far down as the throat; this may last from twenty to thirty seconds.

The rational and the biological mechanism by which the pharmaceutical agents function is not presently known and cannot now be explained to a high degree of accuracy. However, it is theorized with no intention to be bound by such theory, that this family of agents, after administration to the nostrils of a patient dissolve the incipient viral colonies in the sinus cavity area, because of their mucolytic properties (hydrolyzation of mucopolysaccharides), resulting in the release of bisulfite and/or sulfite ions. Once these viral colonies are actively deprived of their polysaccharide food source and consequently drained in or out or otherwise removed from the body, alkalinity is stopped and acidity returns to the sinus area, thus aborting the common cold. The bisulfite and/or sulfite ions appear to be responsible for the observed beneficial therapeutic effects.

The use of this invention is preferably practiced at present using a dilute aqueous solution of sodium bisulfite. Because of the tendency for sodium bisulfite to undergo oxidation when in aqueous solution when oxygen is present, it is presently common and even preferred in using this invention to employ a solution which comprises on a 100% by weight total solution basis:

(a) from about 1 to 10% by weight of dissolved inorganic solids, and (b) the balance up to 100% by weight of any given solution being water.

The water used in such solution is preferably purified (e.g., filtered, deionized, distilled or the like) and, for purposes of nasal application, is preferably isotonic and may contain small quantities of preservatives such as 0.001% thiomersal. After preparation, such a solution is preferably stored in a closed container to reduce oxidation.

A solution of sodium bisulfite is prepared by dissolving pharmaceutical grade (U.S.P. Grade) powdered sodium bisulfite (sodium metabisulfite) in distilled water at room temperature to form a 5% by weight aqueous solution.

This solution is then placed into a series of plastic squeeze bottles, each with a volumetric capacity of about 50-52 ml. Each bottle is provided with a cap permitting drop-wise dispensing of solution from such bottle at an estimated rate of 15 drops per ml. This solution was used in each of the case histories that follow.

The present invention is further illustrated by reference to the following case histories. Those skilled in the art will appreciate that other and further embodiments are obvious and within the spirit and scope of this invention from the teachings of these present examples taken with the accompanying specification.

EXAMPLE I

A woman, age 64, weight 71 Kgms, had an itching sensation inside the nose, one of the preliminary symptoms of the common cold. She lay down and applied two drops of the pharmaceutical solution as prepared above to her left nostril and after one minute, two more drops to her right nostril. About one minute later, she blew her nose. Soon after her itching sensation had disappeared.

EXAMPLE II

A man, age 40, weight 82 Kgms, had a slight runny nose, one of the preliminary symptoms of the common cold. He lay down and applied two drops of the pharmaceutical solution in each of his nostrils with one minute intervals. Two minutes later he blew his nose. His symptoms disappeared immediately.

EXAMPLE III

A boy, age 10, weight 39 Kgms, had two of the preliminary symptoms of the common cold—sneezing and a stuffy feeling in the head. He lay down and one drop of the pharmaceutical solution was applied to each one of his nostrils with one minute intervals. Soon after he blew his nose. He sneezed no more and about one hour later he said his head was clear.

EXAMPLE IV

A girl, age 6, weight 25 Kgms, had some preliminary symptoms of the common cold—itching sensation in the nose, watery eyes and a slight fever. Before going to sleep at night, one drop of the pharmaceutical solution was put in each of her nostrils, while she was in a lying position, with one minute intervals. She then blew her nose. The next day she felt fine.

What is claimed:

1. A method of ameliorating the symptoms and progressive onset of a rhinovirus infection in a person by adjusting the pH of the person's nasal mucosal membrane, comprising administering to the person's nasal mucosa a pH-adjusting and rhinovirus-inhibiting quantity of an isotonic, buffered solution consisting of, as the sole active ingredient, a sodium, potassium, calcium or magnesium sulfite or sodium, potassium, calcium or by magnesium bisulfite salt present in the solution in a concentration of from 1 to 10% weight percent.

2. The method of claim 1 in which the solution is administered drop-wise as a nasal solution.

3. The method of claim 2 in which the solution contains sodium bisulfite.

4. The method of claim 2 in which the solution contains sodium metabisulfite.

5. The method of claim 4 in which from 1–4 drops of a 5 weight percent solution are administered drop-wise into each of the patient's nostrils.

6. The method of claim 1 in which the solution is administered as a nasal spray.

7. The method of claim 6 in which the solution contains sodium bisulfite.

8. The method of claim 6 in which the solution contains sodium metabisulfite.

9. The method of claim 6 in which the equivalent of from 1 to 4 drops of a 5 weight percent solution are sprayed into each of the patient's nostrils.

10. A method of treating the symptoms of the common cold in a person suffering from such symptoms comprising administering to said person a symptom-alleviating amount of a solution consisting essentially of a compound which in aqueous solution furnishes sulfite ions, bisulfite ions or both sulfite and bisulfite ions as the sole active ingredient.

11. The method of claim 10 in which the compound is a sodium, potassium, calcium or magnesium sulfite or bisulfite salt.

12. The method of claim 11 in which the compound is sodium metabisulfite.

13. The method of claim 10 in which said compound is administered intranasally.

* * * * *